United States Patent
Nakatani et al.

(10) Patent No.: US 11,098,330 B2
(45) Date of Patent: Aug. 24, 2021

(54) METHOD FOR PRODUCING ERGOTHIONEINE

(71) Applicant: NAGASE & CO., LTD., Osaka (JP)

(72) Inventors: Takeshi Nakatani, Kobe (JP); Nanami Nakashima, Kobe (JP)

(73) Assignee: NAGASE & CO., LTD., Osaka (JP)

( * ) Notice: Subject to any disclaimer, the term of this patent is extended or adjusted under 35 U.S.C. 154(b) by 0 days.

(21) Appl. No.: 16/971,503

(22) PCT Filed: Feb. 19, 2019

(86) PCT No.: PCT/JP2019/006089
§ 371 (c)(1),
(2) Date: Aug. 20, 2020

(87) PCT Pub. No.: WO2019/163767
PCT Pub. Date: Aug. 29, 2019

(65) Prior Publication Data
US 2020/0385769 A1    Dec. 10, 2020

(30) Foreign Application Priority Data
Feb. 23, 2018  (JP) .............................. JP2018-031164

(51) Int. Cl.
| | | |
|---|---|---|
| C12P 13/08 | (2006.01) | |
| C12N 1/20 | (2006.01) | |
| C12P 13/24 | (2006.01) | |
| C12P 13/04 | (2006.01) | |

(52) U.S. Cl.
CPC ................ C12P 13/08 (2013.01); C12N 1/20 (2013.01); C12P 13/24 (2013.01); C12P 13/04 (2013.01)

(58) Field of Classification Search
CPC ............ C12P 13/04; C12P 13/24; C12P 13/08; C12N 1/20
See application file for complete search history.

(56) References Cited

U.S. PATENT DOCUMENTS

| | | | |
|---|---|---|---|
| 5,438,151 A | 8/1995 | Yadan et al. | |
| 2015/0225755 A1 | 8/2015 | Liu | |
| 2017/0051325 A1 | 2/2017 | Han et al. | |
| 2017/0321235 A1 | 11/2017 | Hara et al. | |

FOREIGN PATENT DOCUMENTS

| | | |
|---|---|---|
| JP | 2006-160748 A | 6/2006 |
| JP | 2007-300916 A | 11/2007 |
| JP | 2016-502859 | 2/2016 |
| JP | 2017-225368 | 12/2017 |
| WO | 2015/168112 | 11/2015 |
| WO | 2016/121285 | 8/2016 |
| WO | 2017/150304 | 9/2017 |
| WO | WO-2017150304 A * | 9/2017 |

OTHER PUBLICATIONS

Chen et al. Pseudomonas syringae BetT is a low-affinity choline transporter that is responsible for superior osmoprotection by choline over glycine betaine. J Bacteriol (2008), 190(8): 2717-2725.*
Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36): 11643-50.*
Chica et al., Semi-rational approaches to engineering enzyme activity: combining the benefits of directed evolution and rational design. Curr. Opi. Biotechnol., 2005, vol. 16: 378-384.*
Osawa et al. Heterologous and High Production of Ergothioneine in Escherichia coli. J. Agric. Food Chem. 2018, 66, 1191-1196, Epub Dec. 25, 2017.*
Jones, et al., The evolutionary history of the genes involved in the biosynthesis of the antioxidant ergothioneine, Gene, vol. 549 (2014), pp. 161-170 (D6).
International Preliminary Report on Patentability and Written Opinion dated Aug. 27, 2020 in PCT/JP2019/006089 filed on Feb. 19, 2019 (with English translation), 9 pages.
International Search Report dated May 7, 2019 in PCT/JP2019/006089 filed on Feb. 19, 2019 (with English translation). 6 pages.

* cited by examiner

*Primary Examiner* — Iqbal H Chowdhury
(74) *Attorney, Agent, or Firm* — Oblon, McClelland, Maier & Neustadt, L.L.P.

(57) ABSTRACT

A method for producing ergothioneine at a low cost in large quantities and a bacterium for use in said method are provided. A method for producing ergothioneine or a related substance thereof, or a mixture thereof, comprising culturing a bacterium belonging to the family Enterobacteriaceae having the ergothioneine-producing ability in a culture medium, and collecting ergothioneine or a related substance thereof, or a mixture thereof, from the culture medium or from the cells obtained by culture, wherein said bacterium is the one which is modified so as to have a reduced activity of a protein comprising a core sequence region comprising 5 amino acid residues: Ser-Arg-Gly-Arg-Thr (SEQ ID NO:7) as a part thereof; and a bacterium belonging to the family Enterobacteriaceae having the ergothioneine-producing ability modified so as to have a reduced activity of a protein comprising a core sequence region comprising 5 amino acid residues: Ser-Arg-Gly-Arg-Thr (SEQ ID NO:7) as a part thereof.

7 Claims, 2 Drawing Sheets

Specification includes a Sequence Listing.

SEQUENCE LISTING

```
<160> NUMBER OF SEQ ID NOS: 13

<210> SEQ ID NO 1
<211> LENGTH: 2322
<212> TYPE: DNA
<213> ORGANISM: Schizosaccaromyces pombe

<400> SEQUENCE: 1
atgaccgaaa tcgaaaacat cggtgctctg gaagttctgt tctctccgga atctatcgaa      60
cagtctctga aacgttgcca gctgccgtct accctgctgt acgacgaaaa aggtctgcgt     120
ctgttcgacg aaatcaccaa cctgaaagaa tactacctgt acgaatctga actggacatc     180
ctgaaaaaat tctctgactc tatcgctaac cagctgctgt ctccggacct gccgaacacc     240
gttatcgaac tgggttgcgg taacatgcgt aaaaccaaac tgctgctgga cgctttcgaa     300
aaaaaaggtt gcgacgttca cttctacgct ctggacctga acgaagctga actgcagaaa     360
ggtctgcagg aactgcgtca gaccaccaac taccagcacg ttaaagtttc tggtatctgc     420
ggttgcttcg aacgtctgct gcagtgcctg gaccgtttcc gttctgaacc gaactctcgt     480
```

| | |
|---|---|
| atctctatgc tgtacctggg tgcttctatc ggtaacttcg accgtaaatc tgctgcttct | 540 |
| ttcctgcgtt ctttcgcttc tcgtctgaac atccacgaca acctgctgat ctctttcgac | 600 |
| caccgtaaca aagctgaact ggttcagctg gcttacgacg acccgtaccg tatcaccgaa | 660 |
| aaattcgaaa aaacatcct ggcttctgtt aacgctgttt tcggtgaaaa cctgttcgac | 720 |
| gaaaacgact gggaatacaa atctgtttac gacgaagacc tgggtgttca ccgtgcttac | 780 |
| ctgcaggcta aaacgaagt taccgttatc aaggtccga tgttcttcca gttcaaaccg | 840 |
| tctcacctga tcctgatcga agaatcttgg aaaaactctg accaggaatg ccgtcagatc | 900 |
| atcgaaaaag gtgacttcaa actggtttct aaatacgaat ctaccatcgc tgactactct | 960 |
| acctacgtta tcaccaaaca gttcccggct atgctgcagc tgccgctgca gccgtgcccg | 1020 |
| tctctggctg aatgggacgc tctgcgtaaa gtttggctgt tcatcaccaa caaactgctg | 1080 |
| aacaaagaca acatgtacac cgcttggatt ccgctgcgtc acccgccgat cttctacatc | 1140 |
| ggtcacgttc cggttttcaa cgacatctac ctgaccaaaa tcgttaaaaa caaagctacc | 1200 |
| gctaacaaaa acacttctg gaatggttc cagcgtggta tcgacccgga catcgaagac | 1260 |
| ccgtctaaat gccactggca ctctgaagtt ccggaatctt ggccgtctcc ggaccagctg | 1320 |
| cgtgaatacg aaaaagaatc ttgggaatac acatcgtta aactgtgcaa agctatggac | 1380 |
| gaactgtcta cctctgaaaa acgtatcctg tggctgtgct acgaacacgt tgctatgcac | 1440 |
| gttgaaacca ccctgtacat ctacgttcag tcttccaga acgctaacca gaccgtttct | 1500 |
| atctgcggtt ctctgccgga accggctgaa aaactgacca agctccgct gtgggttaac | 1560 |
| gttccggaaa ccgaaatcgc tgttggtatg ccgctgacca cccagtacac ctctgttggt | 1620 |
| tctaacctgc agtcttctga cctgtctgct cacgaaaaca ccgacgaact gttctacttc | 1680 |
| gcttgggaca cgaaaaacc gatgcgtaaa aaactggttt cttctttctc tatcgctaac | 1740 |
| cgtccgatct ctaacggtga ataccctggac ttcatcaaca aaaaatctaa accgaacgt | 1800 |
| gtttacccga acagtgggc tgaaatcgac ggtaccctgt acatccgtac catgtacggt | 1860 |
| ctgctgccgc tggacgacta cctgggttgg ccggttatga cctcttacga cgacctgaac | 1920 |
| aactacgctt cttctcaggg ttgccgtctg ccgaccgaag acgaactgaa ctgcttctac | 1980 |
| gaccgtgttc tggaacgtac cgacgaaccg tacgtttcta ccgaaggtaa agctaccggt | 2040 |
| ttccagcagc tgcacccgct ggctctgtct gacaactctt ctaaccagat cttcaccggt | 2100 |
| gcttgggaat ggacctctac cgttctggaa aaacacgaag acttcgaacc ggaagaactg | 2160 |
| tacccggact acaccgtga cttcttcgac ggtaaacaca cgttgttct gggtggttct | 2220 |
| ttcgctaccg ctacccgtat ctctaaccgt cgttcttcc gtaacttcta ccaggctggt | 2280 |
| tacaaatacg cttggatcgg tgctcgtctg gttaaaaact ga | 2322 |

<210> SEQ ID NO 2
<211> LENGTH: 1179
<212> TYPE: DNA
<213> ORGANISM: Schizosaccaromyces pombe

<400> SEQUENCE: 2

| | |
|---|---|
| atggctgaaa caacgtttta cggtcacgaa atgaaaaaac acttcatgct ggacccggac | 60 |
| tacgttaacg ttaacaacgg ttcttgcggt actgaatctc tggctgttta caacaaacac | 120 |
| gttcagctgc tgaaagaagc tcagtctaaa ccggacttca tgtgcaacgc ttacatgccg | 180 |
| atgtacatgg aagctacccg taacgaagtt gctaaactga tcggtgctga ctcttctaac | 240 |
| atcgttttct gcaactctgc taccgacggt atctctaccg ttctgctgac cttcccgtgg | 300 |

```
gaacagaacg acgaaatcct gatgctgaac gttgcttacc cgacctgcac ctacgctgct    360
gacttcgcta aaaaccagca caacctgcgt ctggacgtta tcgacgttgg tgttgaaatc    420
gacgaagacc tgttcctgaa agaagttgaa cagcgtttcc tgcagtctaa accgcgtgct    480
ttcatctgcg acatcctgtc ttctatgccg gttatcctgt tcccgtggga aaaagttgtt    540
aaactgtgca aaaatacaa catcgtttct atcatcgacg gtgctcacgc tatcggtcac    600
atcccgatga acctggctaa cgttgacccg gacttcctgt tcaccaacgc tcacaaatgg    660
ctgaactctc cggctgcttg caccgttctg tacgtttctg ctaaaaacca caacctgatc    720
gaagctctgc cgctgtctta cggttacggt ctgcgtgaaa agaatctat cgctgttgac    780 accctgacca accgtttcgt taactctttc aaacaggacc tgccgaaatt catcgctgtt    840
ggtgaagcta tcaaattccg taaatctatc ggtggtgaag aaaaaatcca gcagtactgc    900
cacgaaatcg ctctgaaagg tgctgaaatc atctctaaag aactgggtac ttctttcatc    960
aaaccgccgt acccggttgc tatggttaac gttgaagttc cgctgcgtaa catcccgtct    1020
atcgaaaccc agaaagtttt ctggccgaaa tacaacacct tcctgcgttt catggaattc    1080
aaaggtaaat tctacacccg tctgtctggt gctgtttacc tggaagaatc tgacttctac    1140
tacatcgcta aagttatcaa agacttctgc tctctgtga                          1179

<210> SEQ ID NO 3
<211> LENGTH: 33
<212> TYPE: DNA
<213> ORGANISM: Artificial
<220> FEATURE:
<223> OTHER INFORMATION: Sp.egt1-Fw primer

<400> SEQUENCE: 3
aaatagctgg tgaatgaccg aaatcgaaaa cat                                 33

<210> SEQ ID NO 4
<211> LENGTH: 35
<212> TYPE: DNA
<213> ORGANISM: Artificial
<220> FEATURE:
<223> OTHER INFORMATION: Sp.egt1-Rv primer

<400> SEQUENCE: 4
agccctcctg gatcctcagt ttttaaccag acgag                               35

<210> SEQ ID NO 5
<211> LENGTH: 27
<212> TYPE: DNA
<213> ORGANISM: Artificial
<220> FEATURE:
<223> OTHER INFORMATION: Sp.egt2-Fw primer

<400> SEQUENCE: 5
ggatccagga gggctagcat ggctgaa                                        27

<210> SEQ ID NO 6
<211> LENGTH: 35
<212> TYPE: DNA
<213> ORGANISM: Artificial
<220> FEATURE:
<223> OTHER INFORMATION: Sp.egt2-Rv primer

<400> SEQUENCE: 6
cgactctaga ggatctcaca gagagcagaa gtctt                               35
```

```
<210> SEQ ID NO 7
<211> LENGTH: 5
<212> TYPE: PRT
<213> ORGANISM: E. coli

<400> SEQUENCE: 7

Ser Arg Gly Arg Thr
1               5

<210> SEQ ID NO 8
<211> LENGTH: 12
<212> TYPE: PRT
<213> ORGANISM: E. coli
<220> FEATURE:
<221> NAME/KEY: Xaa
<222> LOCATION: (2)..(2)
<223> OTHER INFORMATION: Xaa stands for Leu or Ile
<220> FEATURE:
<221> NAME/KEY: Xaa
<222> LOCATION: (5)..(5)
<223> OTHER INFORMATION: Xaa stands for Ile or Val
<220> FEATURE:
<221> NAME/KEY: Xaa
<222> LOCATION: (11)..(11)
<223> OTHER INFORMATION: Xaa stands for Ile or Val

<400> SEQUENCE: 8

Phe Xaa Ala Arg Xaa Ser Arg Gly Arg Thr Xaa Arg
1               5                   10

<210> SEQ ID NO 9
<211> LENGTH: 33
<212> TYPE: PRT
<213> ORGANISM: E. coli
<220> FEATURE:
<221> NAME/KEY: Xaa
<222> LOCATION: (1)..(1)
<223> OTHER INFORMATION: Xaa stands for Glu, Ser or Gly
<220> FEATURE:
<221> NAME/KEY: Xaa
<222> LOCATION: (4)..(4)
<223> OTHER INFORMATION: Xaa stands for Leu, Val or Ser
<220> FEATURE:
<221> NAME/KEY: Xaa
<222> LOCATION: (5)..(5)
<223> OTHER INFORMATION: Xaa stands for Phe or Leu
<220> FEATURE:
<221> NAME/KEY: Xaa
<222> LOCATION: (6)..(6)
<223> OTHER INFORMATION: Xaa stands for Phe or Tyr
<220> FEATURE:
<221> NAME/KEY: Xaa
<222> LOCATION: (8)..(8)
<223> OTHER INFORMATION: Xaa stands for Ala or Gly
<220> FEATURE:
<221> NAME/KEY: Xaa
<222> LOCATION: (11)..(11)
<223> OTHER INFORMATION: Xaa stands for Val, Leu or Ile
<220> FEATURE:
<221> NAME/KEY: Xaa
<222> LOCATION: (12)..(12)
<223> OTHER INFORMATION: Xaa stands for Ala, Ser or Ile
<220> FEATURE:
<221> NAME/KEY: Xaa
<222> LOCATION: (13)..(13)
<223> OTHER INFORMATION: Xaa stands for Trp or Tyr
<220> FEATURE:
<221> NAME/KEY: Xaa
<222> LOCATION: (14)..(14)
<223> OTHER INFORMATION: Xaa stands for Ser or Ala
<220> FEATURE:
<221> NAME/KEY: Xaa
<222> LOCATION: (15)..(15)
<223> OTHER INFORMATION: Xaa stands for Pro or Ile
```

```
<220> FEATURE:
<221> NAME/KEY: Xaa
<222> LOCATION: (16)..(16)
<223> OTHER INFORMATION: Xaa stands for Phe or Gln
<220> FEATURE:
<221> NAME/KEY: Xaa
<222> LOCATION: (17)..(17)
<223> OTHER INFORMATION: Xaa stands for Val or Met
<220> FEATURE:
<221> NAME/KEY: Xaa
<222> LOCATION: (18)..(18)
<223> OTHER INFORMATION: Xaa stands for Gly or Ser
<220> FEATURE:
<221> NAME/KEY: Xaa
<222> LOCATION: (19)..(19)
<223> OTHER INFORMATION: Xaa stands for Leu, Met or Ile
<220> FEATURE:
<221> NAME/KEY: Xaa
<222> LOCATION: (21)..(21)
<223> OTHER INFORMATION: Xaa stands for Leu or Ile
<220> FEATURE:
<221> NAME/KEY: Xaa
<222> LOCATION: (24)..(24)
<223> OTHER INFORMATION: Xaa stands for Ile or Val
<220> FEATURE:
<221> NAME/KEY: Xaa
<222> LOCATION: (30)..(30)
<223> OTHER INFORMATION: Xaa stands for Ile or Val
<220> FEATURE:
<221> NAME/KEY: Xaa
<222> LOCATION: (32)..(32)
<223> OTHER INFORMATION: Xaa stands for Gln or Glu
<220> FEATURE:
<221> NAME/KEY: Xaa
<222> LOCATION: (33)..(33)
<223> OTHER INFORMATION: Xaa stands for Phe or Leu

<400> SEQUENCE: 9

Xaa Trp Thr Xaa Xaa Xaa Trp Xaa Trp Trp Xaa Xaa Xaa Xaa Xaa Xaa
1               5                   10                  15

Xaa Xaa Xaa Phe Xaa Ala Arg Xaa Ser Arg Gly Arg Thr Xaa Arg Xaa
            20                  25                  30

Xaa

<210> SEQ ID NO 10
<211> LENGTH: 677
<212> TYPE: PRT
<213> ORGANISM: E. coli

<400> SEQUENCE: 10

Met Thr Asp Leu Ser His Ser Arg Glu Lys Asp Lys Ile Asn Pro Val
1               5                   10                  15

Val Phe Tyr Thr Ser Ala Gly Leu Ile Leu Leu Phe Ser Leu Thr Thr
            20                  25                  30

Ile Leu Phe Arg Asp Phe Ser Ala Leu Trp Ile Gly Arg Thr Leu Asp
            35                  40                  45

Trp Val Ser Lys Thr Phe Gly Trp Tyr Leu Leu Ala Ala Thr Leu
    50                  55                  60

Tyr Ile Val Phe Val Val Cys Ile Ala Cys Ser Arg Phe Gly Ser Val
65                  70                  75                  80

Lys Leu Gly Pro Glu Gln Ser Lys Pro Glu Phe Ser Leu Ser Trp
            85                  90                  95

Ala Ala Met Leu Phe Ala Ala Gly Ile Gly Ile Asp Leu Met Phe Phe
                100                 105                 110

Ser Val Ala Glu Pro Val Thr Gln Tyr Met Gln Pro Pro Glu Gly Ala
            115                 120                 125
```

Gly Gln Thr Ile Glu Ala Ala Arg Gln Ala Met Val Trp Thr Leu Phe
    130                 135                 140

His Tyr Gly Leu Thr Gly Trp Ser Met Tyr Ala Leu Met Gly Met Ala
145                 150                 155                 160

Leu Gly Tyr Phe Ser Tyr Arg Tyr Asn Leu Pro Leu Thr Ile Arg Ser
                165                 170                 175

Ala Leu Tyr Pro Ile Phe Gly Lys Arg Ile Asn Gly Pro Ile Gly His
            180                 185                 190

Ser Val Asp Ile Ala Ala Val Ile Gly Thr Ile Phe Gly Ile Ala Thr
        195                 200                 205

Thr Leu Gly Ile Gly Val Val Gln Leu Asn Tyr Gly Leu Ser Val Leu
    210                 215                 220

Phe Asp Ile Pro Asp Ser Met Ala Ala Lys Ala Ala Leu Ile Ala Leu
225                 230                 235                 240

Ser Val Ile Ile Ala Thr Ile Ser Val Thr Ser Gly Val Asp Lys Gly
                245                 250                 255

Ile Arg Val Leu Ser Glu Leu Asn Val Ala Leu Ala Leu Gly Leu Ile
            260                 265                 270

Leu Phe Val Leu Phe Met Gly Asp Thr Ser Phe Leu Leu Asn Ala Leu
    275                 280                 285

Val Leu Asn Val Gly Asp Tyr Val Asn Arg Phe Met Gly Met Thr Leu
    290                 295                 300

Asn Ser Phe Ala Phe Asp Arg Pro Val Glu Trp Met Asn Asn Trp Thr
305                 310                 315                 320

Leu Phe Phe Trp Ala Trp Trp Val Ala Trp Ser Pro Phe Val Gly Leu
                325                 330                 335

Phe Leu Ala Arg Ile Ser Arg Gly Arg Thr Ile Arg Gln Phe Val Leu
            340                 345                 350

Gly Thr Leu Ile Ile Pro Phe Thr Phe Thr Leu Leu Trp Leu Ser Val
    355                 360                 365

Phe Gly Asn Ser Ala Leu Tyr Glu Ile Ile His Gly Gly Ala Ala Phe
    370                 375                 380

Ala Glu Glu Ala Met Val His Pro Glu Arg Gly Phe Tyr Ser Leu Leu
385                 390                 395                 400

Ala Gln Tyr Pro Ala Phe Thr Phe Ser Ala Ser Val Ala Thr Ile Thr
                405                 410                 415

Gly Leu Leu Phe Tyr Val Thr Ser Ala Asp Ser Gly Ala Leu Val Leu
            420                 425                 430

Gly Asn Phe Thr Ser Gln Leu Lys Asp Ile Asn Ser Asp Ala Pro Gly
    435                 440                 445

Trp Leu Arg Val Phe Trp Ser Val Ala Ile Gly Leu Leu Thr Leu Gly
450                 455                 460

Met Leu Met Thr Asn Gly Ile Ser Ala Leu Gln Asn Thr Thr Val Ile
465                 470                 475                 480

Met Gly Leu Pro Phe Ser Phe Val Ile Phe Phe Val Met Ala Gly Leu
                485                 490                 495

Tyr Lys Ser Leu Lys Val Glu Asp Tyr Arg Arg Glu Ser Ala Asn Arg
            500                 505                 510

Asp Thr Ala Pro Arg Pro Leu Gly Leu Gln Asp Arg Leu Ser Trp Lys
        515                 520                 525

Lys Arg Leu Ser Arg Leu Met Asn Tyr Pro Gly Thr Arg Tyr Thr Lys
    530                 535                 540

Gln Met Met Glu Thr Val Cys Tyr Pro Ala Met Glu Glu Val Ala Gln

```
            545                 550                 555                 560
Glu Leu Arg Leu Arg Gly Ala Tyr Val Glu Leu Lys Ser Leu Pro Pro
                565                 570                 575

Glu Glu Gly Gln Gln Leu Gly His Leu Asp Leu Leu Val His Met Gly
            580                 585                 590

Glu Glu Gln Asn Phe Val Tyr Gln Ile Trp Pro Gln Gln Tyr Ser Val
        595                 600                 605

Pro Gly Phe Thr Tyr Arg Ala Arg Ser Gly Lys Ser Thr Tyr Tyr Arg
    610                 615                 620

Leu Glu Thr Phe Leu Leu Glu Gly Ser Gln Gly Asn Asp Leu Met Asp
625                 630                 635                 640

Tyr Ser Lys Glu Gln Val Ile Thr Asp Ile Leu Asp Gln Tyr Glu Arg
                645                 650                 655

His Leu Asn Phe Ile His Leu His Arg Glu Ala Pro Gly His Ser Val
            660                 665                 670

Met Phe Pro Asp Ala
        675

<210> SEQ ID NO 11
<211> LENGTH: 504
<212> TYPE: PRT
<213> ORGANISM: E. coli

<400> SEQUENCE: 11

Met Lys Asn Glu Lys Arg Lys Thr Gly Ile Glu Pro Lys Val Phe Phe
1               5                   10                  15

Pro Pro Leu Ile Ile Val Gly Ile Leu Cys Trp Leu Thr Val Arg Asp
            20                  25                  30

Leu Asp Ala Ala Asn Val Val Ile Asn Ala Val Phe Ser Tyr Val Thr
        35                  40                  45

Asn Val Trp Gly Trp Ala Phe Glu Trp Tyr Met Val Val Met Leu Phe
    50                  55                  60

Gly Trp Phe Trp Leu Val Phe Gly Pro Tyr Ala Lys Lys Arg Leu Gly
65                  70                  75                  80

Asn Glu Pro Pro Glu Phe Ser Thr Ala Ser Trp Ile Phe Met Met Phe
                85                  90                  95

Ala Ser Cys Thr Ser Ala Ala Val Leu Phe Trp Gly Ser Ile Glu Ile
            100                 105                 110

Tyr Tyr Tyr Ile Ser Thr Pro Pro Phe Gly Leu Glu Pro Asn Ser Thr
        115                 120                 125

Gly Ala Lys Glu Leu Gly Leu Ala Tyr Ser Leu Phe His Trp Gly Pro
    130                 135                 140

Leu Pro Trp Ala Thr Tyr Ser Phe Leu Ser Val Ala Phe Ala Tyr Phe
145                 150                 155                 160

Phe Phe Val Arg Lys Met Glu Val Ile Arg Pro Ser Ser Thr Leu Val
                165                 170                 175

Pro Leu Val Gly Glu Lys His Ala Lys Gly Leu Phe Gly Thr Ile Val
            180                 185                 190

Asp Asn Phe Tyr Leu Val Ala Leu Ile Phe Ala Met Gly Thr Ser Leu
        195                 200                 205

Gly Leu Ala Thr Pro Leu Val Thr Glu Cys Met Gln Trp Leu Phe Gly
    210                 215                 220

Ile Pro His Thr Leu Gln Leu Asp Ala Ile Ile Ile Thr Cys Trp Ile
225                 230                 235                 240
```

```
Ile Leu Asn Ala Ile Cys Val Ala Cys Gly Leu Gln Lys Gly Val Arg
                245                 250                 255

Ile Ala Ser Asp Val Arg Ser Tyr Leu Ser Phe Leu Met Leu Gly Trp
            260                 265                 270

Val Phe Ile Val Ser Gly Ala Ser Phe Ile Met Asn Tyr Phe Thr Asp
        275                 280                 285

Ser Val Gly Met Leu Leu Met Tyr Leu Pro Arg Met Leu Phe Tyr Thr
    290                 295                 300

Asp Pro Ile Ala Lys Gly Phe Pro Gln Gly Trp Thr Val Phe Tyr
305                 310                 315                 320

Trp Ala Trp Trp Val Ile Tyr Ala Ile Gln Met Ser Ile Phe Leu Ala
                325                 330                 335

Arg Ile Ser Arg Gly Arg Thr Val Arg Glu Leu Cys Phe Gly Met Val
            340                 345                 350

Leu Gly Leu Thr Ala Ser Thr Trp Ile Leu Trp Thr Val Leu Gly Ser
        355                 360                 365

Asn Thr Leu Leu Leu Ile Asp Lys Asn Ile Ile Asn Ile Pro Asn Leu
    370                 375                 380

Ile Glu Gln Tyr Gly Val Ala Arg Ala Ile Ile Glu Thr Trp Ala Ala
385                 390                 395                 400

Leu Pro Leu Ser Thr Ala Thr Met Trp Gly Phe Phe Ile Leu Cys Phe
                405                 410                 415

Ile Ala Thr Val Thr Leu Val Asn Ala Cys Ser Tyr Thr Leu Ala Met
            420                 425                 430

Ser Thr Cys Arg Glu Val Arg Asp Gly Glu Glu Pro Leu Leu Val
        435                 440                 445

Arg Ile Gly Trp Ser Ile Leu Val Gly Ile Gly Ile Val Leu Leu
    450                 455                 460

Ala Leu Gly Gly Leu Lys Pro Ile Gln Thr Ala Ile Ile Ala Gly Gly
465                 470                 475                 480

Cys Pro Leu Phe Phe Val Asn Ile Met Val Thr Leu Ser Phe Ile Lys
                485                 490                 495

Asp Ala Lys Gln Asn Trp Lys Asp
            500

<210> SEQ ID NO 12
<211> LENGTH: 973
<212> TYPE: DNA
<213> ORGANISM: Streptomyces coelicolor

<400> SEQUENCE: 12
atgagccaat tccgcttgac ccgcacactg cccgaagatg ctaccgatgc tgccttacgc      60
gccgatgtac tggcgggact gacctccacg cccaaatggt tgccgccgaa atggttctat     120
gacgcgcgtg gtcggaact gtttgaagca atcacggcac tgcctgagta ctacccaacg     180
cgtgctgaac gcgagattct cgtcgatcgt gcaggggaaa ttgcggctgc cacaggtgcc     240
cgcactctcg tggagttggg ttcaggcagt agcgagaaaa cccgtgtcct cctggatgcc     300
ctgaccgaac gtaatgggtt acgcggctat gtgcctgtgg atgtttcgga aagcgcgctg     360
gttcaggctg acaggcgtt agtggcagaa cgtccgggct acaggtcca tgcgctgatt     420 gccgacttca ctggcggtct gactctgccg gacaccccag gtccgcggtt agtcgctttt     480
ctgggtggca caattggcaa cttactgccg ggtgaacggg cagagttcct ggcaagcgtt     540
cgctcactgc tgtctccagg tgatacgctt ctgctgggca cggacttggt gaaagacgaa     600
```

```
ggggttctcg tgcgcgcgta tgatgatgcc gcgggagtta cgggcgagtt caacaagaac    660
gtactgagcg tggttaatcg cgaactggaa gccgactttg ccccggcggc gtttgaacac    720
gtagcgttgt ggaatgcgga acgggaatgg atcgaaatgc gcctgcgttc tcgtaccgcc    780
caagcggtga aaatccaggc actggatctg gcagtggact ttgccgatgg tgaagagttg    840
cgtaccgagg tcagtgcgaa grtttcgccg cgaaggcgta cgcgcagaac ttgccgctgc    900
cggccttgat ctggcgcatt ggtggaccga tggtggcgac cgttttgcac tttccctctc    960
ggttgcgcgc taa                                                       973

<210> SEQ ID NO 13
<211> LENGTH: 1374
<212> TYPE: DNA
<213> ORGANISM: Chlorobium limicola

<400> SEQUENCE: 13
atgcagaaca aaatttccg tgccccacaa agcgaagcca ttggcatcct gtacaagctc     60
atagaaactg gctccaaaca caaaaacatg tatgaccaca cggaaatcac cacagactca    120
ctgctggcgc tgttaggtag cgaaaaggtc aaaatcattg atgtccgcag tgcggatgcg    180
tataacggtt ggcgtatgag aggggaggta cgtggtggcc atatcaaagg cgcaaaatcg    240
ctgccagcga atggctcac agatccggaa tggttaaaca ttgtgcgctt aaacagatt     300 cgaccagaag atgcgattgt gctctatggg tatacgcctg aagaatgcga acagactgct    360 actcgctttta aggagaatgg ctacaacaac gtttcggtgt ccatcgctt tcatccggat    420 tggaccggga atgatgcctt ccctatggac cgcttggaac agtacaaccg tttagtgcct    480
gccgaatggg tcaatggtct gatctctggc gaagaaatcc ggagtatga caacgatacc    540 ttcatcgtgt gtcatgcgca ttaccggaat cgtgatgcct accttagcgg gcatattccg    600
ggagcaacgg acatggacac tctggctctt gagtctccgg aaacctggaa tcgtcgcaca    660
ccagaagagc tgaaaaaagc gcttgaggaa cacggtatta ccgcaagcac caccgtggtt    720
ctgtacggca aattcatgca tccggataat gcggatgaat tccgggaag tgctgctgga    780 cacataggag cgattcgtct ggcgtttatc atgatgtatg caggcgtgga ggatgttcgc    840
gtgttgaatg gcggctatca gtcatggacg gatgcaggct ttgccatcag taaggatgat    900
gttcccaaaa ccaccgtacc ggagtttggt gcgccgattc cgtcacgtcc ggaatttgcg    960
gtagacattg acgaagctaa agatgctg caatcggaag actctgattt ggtctgcgtt    1020
cggtcctatc ccgaatacat tggggaagtg agcggctaca actatatcaa gaaaaaaggt    1080
aggattcctg cgccattttt cgctgaatgc ggttccgatg cataccacat ggagaattat    1140
cgcaaccatg atcacacgac ccgcgagtat cacgaaatcg aggacatttg gccaaaagt    1200 gggatcattc cgaagaaaca tctggccttc tactgtggta cggttggcg tggttcggaa    1260 gcatggttta acgcgctact gatgggttgg ccgcgcgtca gcgtatatga tggtggctgg    1320
tttgaatgga gcaatgaccc cgaaaaccg tatgaaaccg gcgttccaaa ataa           1374
```

METHOD FOR PRODUCING ERGOTHIONEINE

TECHNICAL FIELD

The present invention relates to a method for producing ergothioneine or a related substance thereof, or a mixture thereof, using a bacterium belonging to the family Enterobacteriaceae. The present invention enhances the ergothioneine-producing ability of a bacterium belonging to the family Enterobacteriaceae having said ability by modification thereof to reduce the activity of a given protein.

BACKGROUND ART

Ergothioneine is a kind of sulfur-containing amino acid and is known to have various physiological activities such as antioxidant ability. It is also suggested that its antioxidant ability is higher than that of vitamin C, vitamin E, cysteine and glutathione. It has also been shown that ergothioneine has an ultraviolet absorption effect, a melanin production inhibitory activity, a scavenging ability to reactive oxygen species, an elastase activity inhibitory activity that suppresses the formation of wrinkles and sagging, and a tyrosinase activity inhibitory activity that suppresses the formation of spots. Therefore, ergothioneine is one of the compounds that receive a lot of attention especially in the field of cosmetic and food industries.

Ergothioneine is abundant in some microorganisms, especially basidiomycetes, and is also present in trace amounts in plants and animals. Although mammals cannot biosynthesize ergothioneine, it is suggested that they can take up ergothioneine into the body by feeding mushrooms including basidiomycetes and that ergothioneine accumulates in many organs such as epidermis, brain, liver, kidney, spinal cord and eyes to protect cells. For production of ergothioneine, a method for culture and extraction of microorganisms such as basidiomycetes and a method for organic synthesis are known (cf. Patent references 1 and 2). However, the method for extraction from basidiomycetes has not yet come into widespread use due to various reasons such as its low productivity, a long period of time for culturing microorganisms, a complicated manufacturing process for extraction from within the cells due to its accumulation within the cells, and difficulty in improving the microorganisms. Also, the organic synthetic method has not yet come into widespread use due to various reasons such as complexity of multi-step reaction, possible use of a harmful raw material, and a high cost due to the use of an expensive raw material. A fermentation production method using a microorganism overexpressing ergothioneine biosynthesis genes or a microorganism having the ergothioneine-producing ability in which the histidine ammonia lyase activity is reduced or eliminated or the expression of histidine ammonia lyase gene is reduced or eliminated has been developed, but a more efficient method for producing ergothioneine is desired (Patent reference 3).

PRIOR ART

Patent Reference

Patent reference 1: JP 2006-160748
Patent reference 2: JP 2007-300916
Patent reference 3: WO2017150304

DISCLOSURE OF THE INVENTION

Technical Problem to be Solved by the Invention

As described above, under existing conditions, ergothioneine is expensive and its supply is problematic. Therefore, there is a need for a method for producing ergothioneine at a low cost in large quantities.

Means for Solving the Problems

The present inventors have earnestly studied to solve the above problems, and as a result, surprisingly have found that a production level of ergothioneine can significantly increase by modifying bacteria belonging to the family Enterobacteriaceae having the ergothioneine-producing ability so as to reduce the activity of a given protein to thereby complete the present invention.

Namely, the present invention provides a method for producing ergothioneine or a related substance thereof, or a mixture thereof, using a bacterium belonging to the family Enterobacteriaceae and enhances the ergothioneine-producing ability of a bacterium belonging to the family Enterobacteriaceae having said ability by modification thereof to reduce the activity of a given protein.

Thus, the present invention provides the followings.

[1] A method for producing ergothioneine or a related substance thereof, or a mixture thereof, comprising culturing a bacterium belonging to the family Enterobacteriaceae having the ergothioneine-producing ability in a culture medium, and collecting ergothioneine or a related substance thereof, or a mixture thereof, from the culture medium or from the cells obtained by culture, wherein said bacterium is the one which is modified so as to have a reduced activity of a protein comprising a core sequence region comprising 5 amino acid residues: Ser-Arg-Gly-Arg-Thr (SEQ ID NO:7) as a part thereof.

[2] The method of [1] wherein the core sequence region has the sequence:

```
Phe-X15aa-Ala-Arg-X16aa-Ser-Arg-Gly-Arg-Thr-X17aa-
Arg
``` wherein X15aa, X16aa and X17aa are arbitrary amino acid residues (SEQ ID NO: 8).

[3] The method of [2] wherein the core sequence region is the sequence having the amino acid residues selected from the following (1) to (3):
(1) X15aa is Leu or Ile;
(2) X16aa is Ile or Val;
(3) X17aa is Ile or Val.

[4] The method of [1] wherein the protein comprising a core sequence region is either a BetT protein or a CaiT protein, or both, wherein the BetT protein is the protein of (a), (b), or (c) below and wherein the CaiT protein is the protein of (d), (e), or (f) below:
(a) a protein comprising the amino acid sequence shown in SEQ ID NO: 10;
(b) a protein comprising the amino acid sequence shown in SEQ ID NO: 10 wherein one to several amino acid residue(s) is/are substituted, deleted, inserted or added;
(c) a protein comprising an amino acid sequence having 90% or more identity to the amino acid sequence shown in SEQ ID NO: 10;
(d) a protein comprising the amino acid sequence shown in SEQ ID NO: 11;

(e) a protein comprising the amino acid sequence shown in SEQ ID NO: 11 wherein one to several amino acid residue(s) is/are substituted, deleted, inserted or added;
(f) a protein comprising an amino acid sequence having 90% or more identity to the amino acid sequence shown in SEQ ID NO: 11.

[5] The method of any one of [1] to [4] wherein the bacterium belonging to the family Enterobacteriaceae having the ergothioneine-producing ability is a bacterium modified so as to enhance the expression of ergothioneine biosynthesis genes.

[6] The method of [5] wherein the ergothioneine biosynthesis genes comprise any one or more of a gene corresponding to egtA, egtB, egtC, egtD or egtE of *Mycobacterium smegmatis*, a gene corresponding to Egt1 or Egt2 of *Shizosaccaromyces pombe*, a gene corresponding to Egt1 or Egt2 of *Neurospora crassa*, a gene corresponding to eanA or eanB of *Chlorobium limicola*.

[7] The method of any one of [1] to [6] wherein the bacterium belonging to the family Enterobacteriaceae having the ergothioneine-producing ability is a bacterium belonging to the genus *Escherichia*.

[8] The method of [7] wherein the bacterium belonging to the family Enterobacteriaceae having the ergothioneine-producing ability is *Escherichia coli*.

[9] A bacterium belonging to the family Enterobacteriaceae having the ergothioneine-producing ability modified so as to have a reduced activity of a protein comprising a core sequence region comprising 5 amino acid residues: Ser-Arg-Gly-Arg-Thr (SEQ ID NO:7) as a part thereof.

[10] The bacterium of [9] wherein the core sequence region has the sequence:

```
Phe-X15aa-Ala-Arg-X16aa-Ser-Arg-Gly-Arg-Thr-X17aa-
Arg
``` wherein X15aa, X16aa and X17aa are arbitrary amino acid residues (SEQ ID NO: 8).

[11] The bacterium of [10] wherein the core sequence region is the sequence having the amino acid residue selected from the following (1) to (3):
(1) X15aa is Leu or Ile;
(2) X16aa is Ile or Val;
(3) X17aa is Ile or Val.

[12] The bacterium of [9] wherein the protein comprising a core sequence region is either a BetT protein or a CaiT protein, or both, wherein the BetT protein is the protein of (a), (b), or (c) below and wherein the CaiT protein is the protein of (d), (e), or (f) below:
(a) a protein comprising the amino acid sequence shown in SEQ ID NO: 10;
(b) a protein comprising the amino acid sequence shown in SEQ ID NO: 10 wherein one to several amino acid residue(s) is/are substituted, deleted, inserted or added;
(c) a protein comprising an amino acid sequence having 90% or more identity to the amino acid sequence shown in SEQ ID NO: 10;
(d) a protein comprising the amino acid sequence shown in SEQ ID NO: 11;
(e) a protein comprising the amino acid sequence shown in SEQ ID NO: 11 wherein one to several amino acid residue(s) is/are substituted, deleted, inserted or added;
(f) a protein comprising an amino acid sequence having 90% or more identity to the amino acid sequence shown in SEQ ID NO: 11.

[13] The bacterium of any one of [9] to [12] wherein the bacterium is a bacterium modified so as to enhance the expression of ergothioneine biosynthesis genes.

[14] The bacterium of [13] wherein the ergothioneine biosynthesis genes comprise any one or more of a gene corresponding to egtA, egtB, egtC, egtD or egtE of *Mycobacterium smegmatis*, a gene corresponding to Egt1 or Egt2 of *Shizosaccaromyces pombe*, a gene corresponding to Egt1 or Egt2 of *Neurospora crassa*, a gene corresponding to eanA or eanB of *Chlorobium limicola*.

[15] The bacterium of any one of [9] to [14] wherein the bacterium is a bacterium belonging to the genus *Escherichia*.

[16] The bacterium of [15] wherein the bacterium is *Escherichia coli*.

Effects of the Invention

The present invention has made it possible to produce ergothioneine having various physiological activities such as a potent antioxidant activity at a low cost in large quantities.

BEST MODE FOR CARRYING OUT THE INVENTION

Detailed Explanation of the Invention

In the first aspect, the present invention relates to a method for producing ergothioneine (hereinafter also referred to as "EGT") or a related substance thereof, or a mixture thereof, comprising culturing a bacterium belonging to the family Enterobacteriaceae having the EGT-producing ability in a culture medium, and collecting EGT or a related substance thereof, or a mixture thereof, from the culture medium or from the cells obtained by culture, wherein said bacterium is the one which is modified so as to have a reduced activity of a given protein. In accordance with the present invention, by making modification resulting in reduction in the activity of a given protein in a bacterium belonging to the family Enterobacteriaceae having the EGT-producing ability, EGT production level can dramatically increase.

In accordance with the present invention, modification is made to a bacterium belonging to the family Enterobacteriaceae having the EGT-producing ability so as to increase the EGT production level in the culture of said bacterium. Specifically, the modification is made so that the bacterium has a reduced activity of a protein comprising a core sequence region comprising 5 amino acid residues: Ser-Arg-Gly-Arg-Thr (SEQ ID NO:7) as a part thereof.

The protein comprising a core sequence region as mentioned above may be a protein comprising the sequence:

Phe-X15aa-Ala-Arg-X16aa-Ser-Arg-Gly-Arg-Thr-X17aa-Arg wherein X15aa, X16aa and X17aa are arbitrary amino acid residues (SEQ ID NO: 8) as a core sequence region. A core sequence region is preferably the sequence having the amino acid residue selected from the following (1) to (3):
(1) X15aa is Leu or Ile;
(2) X16aa is Ile or Val;
(3) X17aa is Ile or Val.

Furthermore, the protein comprising a core sequence region as mentioned above may be a protein comprising the sequence:

X1aa-Trp-Thr-X2aa-X3aa-X4aa-Trp-X5aa-Trp-Trp-X6aa-X7aa-X8aa-X9aa-X10aa-X11aa-X12aa-X13aa-X14aa-Phe-X15aa-Ala-Arg-X16aa-Ser-Arg-Gly-Arg-Thr-X17aa-Arg-X18aa-X19aa wherein X1aa, X2aa, X3aa, X4aa, X5aa, X6aa, X7aa, X8aa, X9aa, X10aa, X11aa, X12aa, X13aa, X14aa, X11aa, X16aa, X17aa, X18aa and X19aa are arbitrary amino acid residues (SEQ ID NO: 9) as a core sequence region. A core sequence region is preferably a sequence having the amino acid residue selected from the following (1) to (19):
(1) X1aa is Glu, Ser or Gly;
(2) X2aa is Leu, Val or Ser;
(3) X3aa is Phe or Leu;
(4) X4aa is Phe or Tyr;
(5) X5aa is Ala or Gly;
(6) X6aa is Val, Leu or Ile;
(7) X7aa is Ala, Ser or Ile;
(8) X8aa is Trp or Tyr;
(9) X9aa is Ser or Ala;
(10) X10aa is Pro or Ile;
(11) X11aa is Phe or Gln;
(12) X12aa is Val or Met;
(13) X13aa is Gly or Ser;
(14) X14aa is Leu, Met or Ile;
(15) X15aa is Leu or Ile;
(16) X16aa is Ile or Val;
(17) X17aa is Ile or Val;
(18) X18aa is Gln or Glu;
(19) X19aa is Phe or Leu.

Specific examples of the protein comprising a core sequence region include a BetT protein and a CaiT protein wherein the BetT protein is the protein of (a), (b), or (c) below and wherein the CaiT protein is the protein of (d), (e), or (f) below:

(a) a protein comprising the amino acid sequence shown in SEQ ID NO: 10;
(b) a protein comprising the amino acid sequence shown in SEQ ID NO: 10 wherein one to several amino acid residue(s) is/are substituted, deleted, inserted or added;
(c) a protein comprising an amino acid sequence having 90% or more identity to the amino acid sequence shown in SEQ ID NO: 10;
(d) a protein comprising the amino acid sequence shown in SEQ ID NO: 11;
(e) a protein comprising the amino acid sequence shown in SEQ ID NO: 11 wherein one to several amino acid residue(s) is/are substituted, deleted, inserted or added;
(f) a protein comprising an amino acid sequence having 90% or more identity to the amino acid sequence shown in SEQ ID NO: 11.

The protein comprising a core sequence region is preferably a BetT protein comprising an amino acid sequence having 90% or more, 95% or more, or 98% or more identity to the amino acid sequence shown in SEQ ID NO: 10, a CaiT protein comprising an amino acid sequence having 90% or more, 95% or more, or 98% or more identity to the amino acid sequence shown in SEQ ID NO: 11.

As used herein, "one to several amino acid residue(s) is/are substituted, deleted, inserted or added" means that 1, 2, 3, 4, 5, 6, 7, 8, 9 or 10 amino acid residue(s) is/are substituted, deleted, inserted or added, preferably 1, 2, 3, 4, 5 or 6 amino acid residue(s) is/are substituted, deleted, inserted or added, more preferably 1, 2, 3 or 4 amino acid residue(s) is/are substituted, deleted, inserted or added.

As used herein, a "related substance of EGT" means an EGT analog and includes an oxidized EGT, an alkylated EGT, and the like. Specific examples of oxidized EGT include Ergothioneine sulfenic acid, Ergothioneine sulfinic acid, Ergothioneine sulfonic acid, disulfide bound EGT, mixed disulfide EGT, Hercynine, and the like. Examples of an alkylated EGT include S-Methyl-Ergothioneine, and the like. It has been reported that an oxidized EGT and an alkylated EGT as mentioned above are generated from ergothioneine via an intracellular metabolic reaction or an oxidative reaction with oxygen or an oxidant in the culture medium (described in L. Servillo et al., Free. Radic. Biol. Med., 2015, 79, 228-36, and R. M. Y. Tang, et al., Sci. Rep., 2018, 8(1), 1601). Also, an EGT analog includes selenoneine, and the like.

By making the above-mentioned modification to a bacterium belonging to the family Enterobacteriaceae having the EGT-producing ability, i.e. the modification allowing for reduction in the activity of a protein comprising a given core sequence region, it becomes possible to dramatically increase the EGT production level.

A bacterium belonging to the family Enterobacteriaceae having the EGT-producing ability for use in the present invention is the one modified so as to have a reduced activity of a protein comprising a core sequence region comprising 5 amino acid residues: Ser-Arg-Gly-Arg-Thr (SEQ ID NO:7) as a part thereof, the one modified so as to have a reduced activity of a protein comprising the sequence:

Phe-X15aa-Ala-Arg-X16aa-Ser-Arg-Gly-Arg-Thr-X17aa-Arg wherein X11aa, X16aa and X17aa are arbitrary amino acid residues (SEQ ID NO: 8) as a core sequence region, or the one modified so as to have a reduced activity of a protein comprising the sequence:

X1aa-Trp-Thr-X2aa-X3aa-X4aa-Trp-X5aa-Trp-Trp-X6aa-
X7aa-X8aa-X9aa-X10aa-X11aa-X12aa-X13aa-X14aa-Phe-
X15aa-Ala-Arg-X16aa-Ser-Arg-Gly-Arg-Thr-X17aa-Arg-
X18aa-X19aa wherein X1aa, X2aa, X3aa, X4aa, X5aa, X6aa, X7aa, X8aa, X9aa, X11aa, X11aa, X12aa, X13aa, X14aa, X11aa, X16aa, X17aa, X18aa and X19aa are arbitrary amino acid residues (SEQ ID NO: 9) as a core sequence region, preferably the one modified so as to have a reduced activity of a BetT protein or a CaiT protein or a protein comprising an amino acid sequence having 90% or more identity to the amino acid sequence of a BetT protein or a CaiT protein. The rate of reduction of the activity of a BetT protein or a CaiT protein is preferably 50% or less, more preferably 25% or less, even more preferably 10% or less than its parent strain. The bacterium having the eliminated activity of a BetT protein or a CaiT protein is most preferable. The bacterium having the eliminated activity of a BetT protein or a CaiT protein is a bacterium in which the activity of a BetT protein or a CaiT protein is not detected at all. In other words, the bacterium having the reduced or eliminated activity of a BetT protein or a CaiT protein is a bacterium in which the expression of a BetT protein or CaiT protein gene is reduced or eliminated. The rate of reduction of the expression of a BetT protein or CaiT protein gene is preferably 50% or less, more preferably 25% or less, even more preferably 10% or less than its parent strain. The bacterium having the eliminated expression of a BetT protein or CaiT protein gene is most preferable. The bacterium having the eliminated expression of a BetT protein or CaiT protein gene is a bacterium in which the expression of a BetT protein or CaiT protein gene is not detected at all. The activity of a BetT protein or a CaiT protein and the expression of a BetT protein or CaiT protein gene can be measured by known methods such as Northern blotting, RT-PCR, real-time PCR, and Western blotting.

A method for reducing or eliminating the activity of a BetT protein or a CaiT protein and a method for reducing or eliminating the expression of a BetT protein or CaiT protein gene are also known and include, but are not limited to, e.g. knocking-out or knocking-down of a gene of a BetT protein or a CaiT protein by homologous recombination, mutation treatment, genome editing etc., administering a substance that inhibits a BetT protein or a CaiT protein to bacteria, and the like. Also, the bacterium to be used in the present invention may be the one in which the activity of a BetT protein or a CaiT protein is reduced or eliminated as a result of natural mutation.

A bacterium belonging to the family Enterobacteriaceae having the EGT-producing ability for use in the present invention is preferably a bacterium modified so as to enhance the expression of ergothioneine biosynthesis genes.

An EGT biosynthesis gene is a gene encoding an enzyme involved in EGT biosynthesis. Enzymes involved in EGT biosynthesis and EGT biosynthesis genes are known and, for some of the genes, their nucleotide sequences are also known. Those skilled in the art can appropriately select such EGT biosynthesis genes. The EGT biosynthesis genes to be enhanced include, but are not limited to, e.g. one or more of the genes corresponding to egtA, egtB, egtC, egtD or egtE of *Mycobacterium smegmatis*, either or both of the genes corresponding to Egt1 or Egt2 of *Schizosaccharomyces pombe*, either or both of the genes corresponding to Egt1 or Egt2 of *Neurospora crassa*, or either or both of the genes corresponding to eanA or eanB of *Chlorobium limicola*. With respect to the EGT biosynthesis genes of *Mycobacterium*, F. P. Seebeck, J. Am. Chem. Soc., 2010, 132, 6632-6633 can be referred to. With respect to the EGT biosynthesis genes of *Schizosaccharomyces*, T. Pluskal et al, PLOS ONE., 2014, 9(5), e97774 can be referred to. With respect to the EGT biosynthesis genes of *Neurospora*, W. Hu et al., Org. Lett., 2014, 16, 5382-5385 can be referred to. Also, with respect to the EGT biosynthesis genes of *Streptomyces*, S. Nakajima et al., J. Biosci. Bioeng., 2015, 120, 294-298 can be referred to. With respect to the EGT biosynthesis genes of *Chlorobium*, R. Burn, et al., Angew. Chem. Int. Edit., 2017, 56, 12508-12511 can be referred to. With respect to the EGT biosynthesis genes of various microorganisms, G. W. Jones et al, Gene, 2014, 549, 161-170 can be referred to.

"To enhance the expression of a gene" means that an expression level of a given gene is higher than that of a parent strain. The expression level is preferably twice or more, more preferably five times or more, even more preferably ten times or more higher than that of a parent strain or a wild strain. Quantification of gene expression can be performed by a known method such as Northern blotting or real-time PCR.

A "corresponding gene" is, with regard to a gene that encodes an enzyme that catalyzes a reaction in the EGT biosynthetic pathway of a given microorganism, a gene of another microorganism that encodes an enzyme that catalyzes a reaction in the EGT biosynthetic pathway that is the same as or similar to that in the given microorganism. A given gene and a corresponding gene may have the same nucleotide sequence or different nucleotide sequences. For instance, a given gene and a corresponding gene may have a nucleotide sequence identity of 50% or more, 70% or more, 80% or more, or 90% or more. Furthermore, an enzyme protein encoded by a given gene and an enzyme protein encoded by a corresponding gene may have the same amino acid sequence or different amino acid sequences. For instance, an enzyme protein encoded by a given gene and an enzyme protein encoded by a corresponding gene may have an amino acid sequence identity of 50% or more, 70% or more, 80% or more, or 90% or more.

The expression of EGT biosynthesis genes can be enhanced by using a known method for enhancing gene expression. The most commonly used method is to place EGT biosynthesis genes under the control of a promoter having potent expression. For instance, the expression of EGT biosynthesis genes may be enhanced by introducing into a microorganism an expression vector which incorporates a promoter suitable for the expression of EGT biosynthesis genes and EGT biosynthesis genes, or by incorporating EGT biosynthesis genes into the host genome by homologous recombination etc. For the vector, a plasmid vector or a virus vector can be used. When constructing the vector, constituent elements of the vector such as a promoter, a terminator, a marker gene such as a drug resistance gene or a metabolic enzyme gene can be appropriately selected and used. Methods for introducing genes into bacteria are also known. The gene to be introduced can be introduced into bacteria directly or after incorporation into a vector. Examples of a method for introducing a gene include lipofection, calcium phosphate, the use of polymer, electroporation, particle gun, etc. and these methods may be appropriately selected depending on the type of bacteria to which a gene is introduced and the gene to be introduced. In order to enhance the expression of EGT biosynthesis genes, the expression of endogenous EGT biosynthesis genes may also be induced by deleting a specific gene or region on the genome.

The method for enhancing the expression of EGT biosynthesis genes is not limited to the above methods. In addition, the bacterium used in the present invention may be the one having the enhanced expression of EGT biosynthesis genes as a result of natural mutation. The enhanced expression of EGT biosynthesis genes can be confirmed by a known method such as Northern blotting or real-time PCR. Alternatively, the enhanced expression of EGT biosynthesis genes may be confirmed by actually culturing the bacteria and quantifying EGT produced inside or outside (in the culture solution) the cells.

EGT biosynthesis genes to be enhanced for its expression in bacteria may be of one type or two or more types. A set of genes encoding multiple enzymes involved in EGT biosynthesis may be introduced into bacteria as a cluster. EGT biosynthesis genes from microorganisms of a different genus or species may be introduced to enhance the expression, or EGT biosynthesis genes from microorganisms of the same genus or species may be introduced to enhance the expression. It is preferable to introduce EGT biosynthesis genes from the same genus or a related genus to enhance the expression. It is preferable to introduce EGT biosynthesis genes from the same species or a related species to enhance the expression. It is more preferable to introduce EGT biosynthesis genes from the same species to enhance the expression.

A bacterium belonging to the family Enterobacteriaceae having the EGT-producing ability for use in the present invention includes, but is not limited to, a bacterium of *Escherichia, Enterobacter, Pantoea, Klebsiella*, and *Salmonella*. A particularly preferable enterobacterium includes those of *Escherichia* such as *Escherichia coli, Pantoea* such as *Pantoea ananatis*, and the like.

The culture of a bacterium belonging to the family Enterobacteriaceae in the method for producing EGT of the present invention can be carried out by an ordinary method. Specifically, LB medium, 2×YT medium, NZY medium, M9 medium, SOC medium, YPD medium or the like can be used. The above media can be used to produce EGT, but the media to be used are not limited thereto. The produced EGT may be accumulated inside the cells or may be secreted and accumulated outside the cells (in the culture solution).

EGT inside the cells or EGT released from the cells can be collected by a known method. For instance, the culture can be subjected to solid-liquid separation such as centrifugation or filtration, and the EGT extract can be obtained from inside the cells by solvent extraction, hot water extraction, crushing treatment, or the like. From the EGT extract or the culture supernatant, EGT can be obtained by known chromatography such as ion exchange chromatography, hydrophobic chromatography and gel filtration chromatography.

In the second aspect, the present invention relates to a bacterium belonging to the family Enterobacteriaceae having the EGT-producing ability, which is modified according to the present invention so as to have a reduced activity of a given protein.

A bacterium belonging to the family Enterobacteriaceae having the EGT-producing ability, which is modified according to the present invention so as to have a reduced activity of a given protein, is a bacterium belonging to the family Enterobacteriaceae having the EGT-producing ability, which is modified so as to have a reduced activity of a protein comprising a core sequence region comprising 5 amino acid residues: Ser-Arg-Gly-Arg-Thr (SEQ ID NO:7) as a part thereof, a bacterium belonging to the family Enterobacteriaceae having the EGT-producing ability, which is modified so as to have a reduced activity of a protein comprising the sequence:

```
Phe-X15aa-Ala-Arg-X16aa-Ser-Arg-Gly-Arg-Thr-X17aa-
Arg
``` wherein X15aa, X16aa and X17aa are arbitrary amino acid residues (SEQ ID NO: 8), as a core sequence region, or a bacterium belonging to the family Enterobacteriaceae having the EGT-producing ability, which is modified so as to have a reduced activity of a protein comprising the sequence:

```
X1aa-Trp-Thr-X2aa-X3aa-X4aa-Trp-X5aa-Trp-Trp-X6aa-
X7aa-X8aa-X9aa-X10aa-X11aa-X12aa-X13aa-X14aa-Phe-
X15aa-Ala-Arg-X16aa-Ser-Arg-Gly-Arg-Thr-X17aa-Arg-
X18aa-X19aa
``` wherein X1aa, X2aa, X3aa, X4aa, X5aa, X6aa, X7aa, X8aa, X9aa, X10aa, X11aa, X12aa, X13aa, X14aa, X15aa, X16aa, X17aa, X18aa and X19aa are arbitrary amino acid residues (SEQ ID NO: 9) as a core sequence region, preferably a bacterium belonging to the family Enterobacteriaceae having the EGT-producing ability, which is modified so as to have a reduced activity of a BetT protein or a CaiT protein or a protein comprising an amino acid sequence having 90% or more identity to the amino acid sequence of a BetT protein or a CaiT protein. The reduction of the activity of a BetT protein or a CaiT protein is as described above.

A bacterium belonging to the family Enterobacteriaceae having the EGT-producing ability, which is modified according to the present invention so as to have a reduced activity of a given protein, is preferably a bacterium modified so as to enhance the expression of ergothioneine biosynthesis genes.

A bacterium belonging to the family Enterobacteriaceae having the EGT-producing ability, which is modified according to the present invention so as to have a reduced activity of a given protein and is modified so as to enhance the expression of EGT biosynthesis genes, is preferably, but is not limited to, a bacterium modified so as to enhance the expression of EGT biosynthesis genes by enhancing one or more of the genes corresponding to egtA, egtB, egtC, egtD or egtE of *Mycobacterium smegmatis*, either or both of the genes corresponding to Egt1 or Egt2 of *Schizosaccharomyces pombe*, or either or both of the genes corresponding to Egt1 or Egt2 of *Neurospora crassa*.

A bacterium belonging to the family Enterobacteriaceae having the EGT-producing ability, which is modified according to the present invention so as to have a reduced activity of a given protein, may be, but is not limited to, a bacterium of *Escherichia, Enterobacter, Pantoea, Klebsiella*, and *Salmonella*, and most preferably *Escherichia* such as *Escherichia coli, Pantoea* such as *Pantoea ananatis*, and the like.

The present invention is explained in more detail and specifically with the following Examples, which are not intended to limit the scope of the present invention. Unless otherwise specified, experiments were carried out using the methods described in a collection of standard protocols for molecular biology and applied microbiology, or modified or altered methods thereof. In addition, "%" represents "w/v %" unless otherwise specified.

Example 1

Construction of Vector for EGT Production (Egt1-2):

In order to produce EGT in *Escherichia coli*, the following vector for EGT production was constructed. As EGT biosynthesis genes, egt1 (SPBC1604.01: SEQ ID NO: 1) and egt2 (SPBC660.12c: SEQ ID NO: 2) from *Schizosaccharomyces pombe* were used. Using as a template a vector containing the EGT biosynthesis genes egt1 and egt2 shown in the sequence listing, egt1 and egt2 were amplified using the primers shown in Table 1.

TABLE 1

| Primer | Sequence |
| --- | --- |
| Sp.egt1-Fw | 5'-AAATAGCTGGTGAATGACCGAAATCGAAAACAT-3' (SEQ ID NO: 3) |
| Sp.egt1-Rv | 5'-AGCCCTCCTGGATCCTCAGTTTTTAACCAGACGAG-3' (SEQ ID NO: 4) |
| Sp.egt2-Fw | 5'-GGATCCAGGAGGGCTAGCATGGCTGAA-3' (SEQ ID NO: 5) |
| Sp.egt2-Rv | 5'-CGACTCTAGAGGATCTCACAGAGAGCAGAAGTCTT-3' (SEQ ID NO: 6) |

As an expression vector, pACG was used in which the promoter of an expression vector having the p15A replication origin was modified to the promoter of the gapA gene from *Escherichia coli*, and the drug resistance marker was changed to the tetracycline resistance gene. Using In-Fusion HD cloning Kit (Takara Bio Inc.), the PCR products of egt1 and egt2 were ligated to the HindIII-BamHI site immediately downstream the promoter of pACG to construct pACG-EGT as a vector for EGT production. The In-Fusion reaction was performed according to the protocol provided by Takara Bio Inc.

MG1655 strain (ATCC deposit number: 700926) was used as a wild strain of *Escherichia coli*, and transformation was performed using the constructed pACG-EGT to give an EGT-producing strain (MG1655/pACG-EGT).

Example 2

Test for EGT production in *Escherichia coli*:

Using the EGT production strain MG1655/pACG-EGT constructed in Example 1, a test for EGT fermentation production was conducted. MG1655/pACG obtained by introducing the empty vector pACG into MG1655 strain was used as a control strain. A respective glycerol stock of MG1655/pACG and MG1655/pACG-EGT was added to a test tube containing tetracycline (final concentration of 10 µg/mL) in 3 mL of LB medium (polypeptone 10 g, yeast extract 5 g, NaCl 10 g in medium 1 L), which was subjected to shaking culture at 37° C. at 200 rpm for 15-18 hours until reaching a stationary phase to give a preculture solution. Furthermore, the preculture solution was added to 50 mL of 2×TY medium (polypeptone 16 g, yeast extract 10 g, NaCl 5 g, Glucose 5%, L-Histidine 5 mM, L-Cystine 2.5 mM, L-Methionine 5 mM, tetracycline 10 µg/mL in medium 1 L) in a 500 mL baffled flask to give OD=0.4, which was subjected to main culture by shaking at 37° C. at 160 rpm for 96 hours.

The quantification of EGT was performed as described below. During the main culture, 1 mL of the culture solution was collected at 24, 48, 72, and 96 hours after initiation of culture to evaluate the culture samples. After measuring the microbial cell turbidity (OD600) of the collected culture solution, centrifugation was performed at 14000 rpm for 10 minutes to separate the extracellular culture solution and the precipitate (cells). The precipitate was subjected to hot water extraction (60° C., 10 minutes) to extract intracellular components for use as an intracellular sample. The EGT content in the intracellular sample and in the separated extracellular culture solution (extracellular sample) was measured by HPLC. The conditions of HPLC measurement were as shown in Table 2 below and the quantification was performed based on the EGT peak generated at a retention time of around 10 minutes.

TABLE 2

| Column | Inertsil HILIC (5 µM; 4.6 φ mm × 250 mm) manufactured by GL Sciences Inc. |
| --- | --- |
| Solvent | 100 mM ammonium acetate/acetonitrile/isopropanol/water (2:82:6:10) |
| Gradient condition | Isocratic |
| Detection wavelength | 265 nm |
| Flow rate | 1 mL/min. |
| temperature of column | 40° C. |

Figure 1:
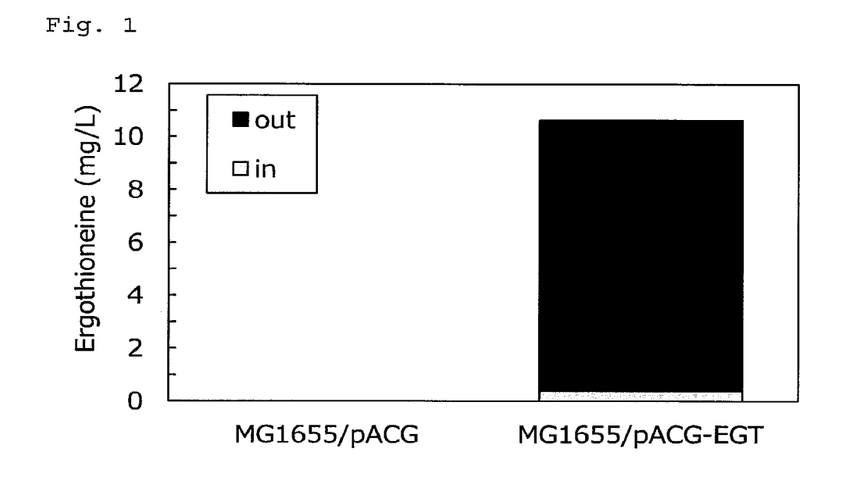
FIG. 1 is a graph showing the results (after 72 hours of culture) of a test for ergothioneine fermentation production using an ergothioneine-producing *Escherichia coli*, MG1655/pACG-EGT. "out" and "in" indicate the EGT content in the culture medium and within the cells, respectively.

As a result of the culture test, after 72 hours of culture, EGT production was not confirmed from the control strain MG1655/pACG, but the peak of peak of EGT could be confirmed in the MG1655/pACG-EGT culture solution and the intracellular extract to confirm EGT synthesis gene-dependent EGT production (FIG. 1).

Example 3

Test for EGT Production in ΔbetT and ΔcaiT:

Next, using the respective gene-disrupted strains of betT and caiT, a test for EGT fermentation production was conducted. The betT gene-disrupted strain (ΔbetT) and the caiT gene-disrupted strain (ΔcaiT) were constructed by a known method of homologous recombination using a counter selection vector (including sacB gene and drug resistance gene) containing upstream and downstream sequences of the betT gene and the caiT gene, respectively, to disrupt the respective genes in the *Escherichia coli* MG1655 strain. For the construction of the above-mentioned disrupted strains, M. S. Donnenberg and J. S. Kaper, Infect. Immun., 1991, 4310-4317, H. Mizoguchi et al., Biosci. Biotechnol. Biochem., 2007, 71 (12), 2905-2911, and the like can be referred to. The constructed ΔbetT and ΔcaiT were transformed with pACG-EGT to give ΔbetT/pACG-EGT and ΔcaiT/pACG-EGT. As a control strain, MG1655/pACG-EGT constructed in Example 2 was used in the following culture test.

Figure 2:
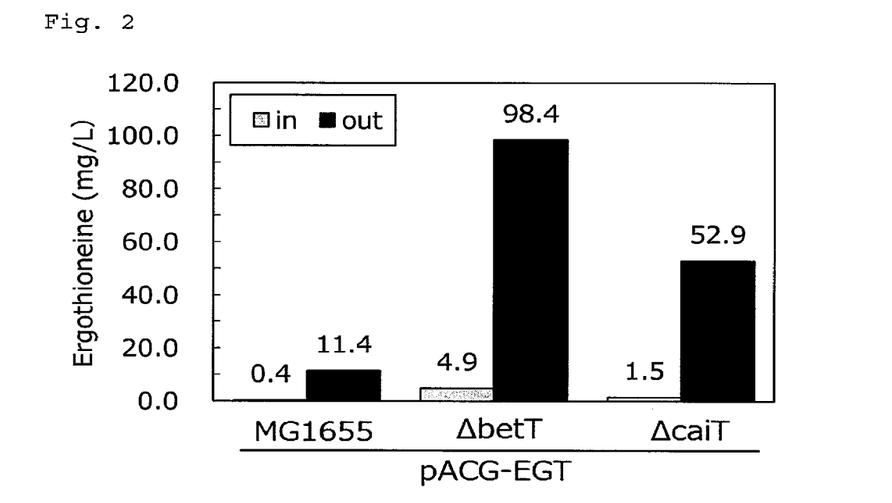
FIG. 2 is a graph showing the results (after 96 hours of culture) of a test for ergothioneine fermentation production using a betT gene-disrupted strain and a caiT gene-disrupted strain, into which pACG-EGT was introduced. "out" and "in" indicate the EGT content in the culture medium and within the cells, respectively.
Figure 3:
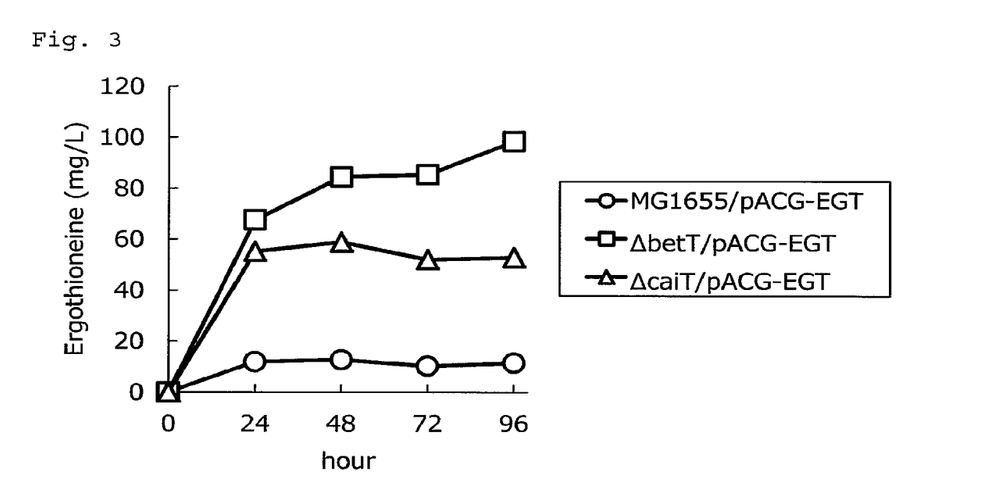
FIG. 3 is a graph showing the results (time course of EGT production level in culture medium) of a test for ergothioneine fermentation production using a betT gene-disrupted strain and a caiT gene-disrupted strain, into which pACG-EGT was introduced.

The culture and the EGT analysis were performed as described in Example 2. As a result of the culture test, the EGT production level in the culture solution 96 hours after initiation of the culture resulted in surprisingly drastic increase both intracellularly and extracellularly in both gene-disrupted strains, ΔbetT/pACG-EGT by about 8.6 times (12.3 times intracellularly) and ΔcaiT/pACG-EGT by about 4.6 times (3.75 times intracellularly), as compared to the wild strain (FIGS. 2 and 3).

Example 4

Construction of Vector for EGT Production (egtD-eanB):

A vector for production was constructed using EGT synthesis genes from anaerobic bacteria. In addition to the enzyme encoded by the egtD gene, the expression in *Escherichia coli* of the enzyme encoded by the eanB gene found in anaerobic bacteria allows for biosynthesis of EGT utilizing the sulfur from thiosulfate ion. For the egtD gene, the nucleotide sequence (SEQ ID NO: 12) obtained by codon-optimizing the amino acid sequence from *Streptomyces coelicolor*, which was classified into the same *Actinomycetales* as *Mycobacterium smegmatis*, was used, and for the eanB gene, the nucleotide sequence (SEQ ID NO: 13) obtained by codon-optimizing the amino acid sequence from the anaerobic bacterium *Chlorobium limicola* was used. The above two genes were artificially synthesized. For the vector, pACG-EGT constructed in Example 1 was used. The vector pACG-EGT was treated with restriction enzymes HindIII-BamHI to cleave the egt1 gene and the artificially synthesized egtD gene was linked to the HindIII-BamHI site by ligation. The vector cloned for the egtD gene was further treated with NheI-XbaI to cleave the egt2 and the eanB gene was linked to the NheI-XbaI site by ligation to construct pACG_egtD-eanB in which egtD-eanB was cloned downstream the gapA promoter.

Example 5

Test for EGT Production Using Vector for EGT Production (egtD-eanB):

Three *Escherichia coli* strains, MG1655, and ΔbetT and ΔcaiT prepared in Example 3, were transformed with pACG_egtD-eanB constructed in Example 4, and the obtained strains were used in the following test for EGT production.

Figure 4:
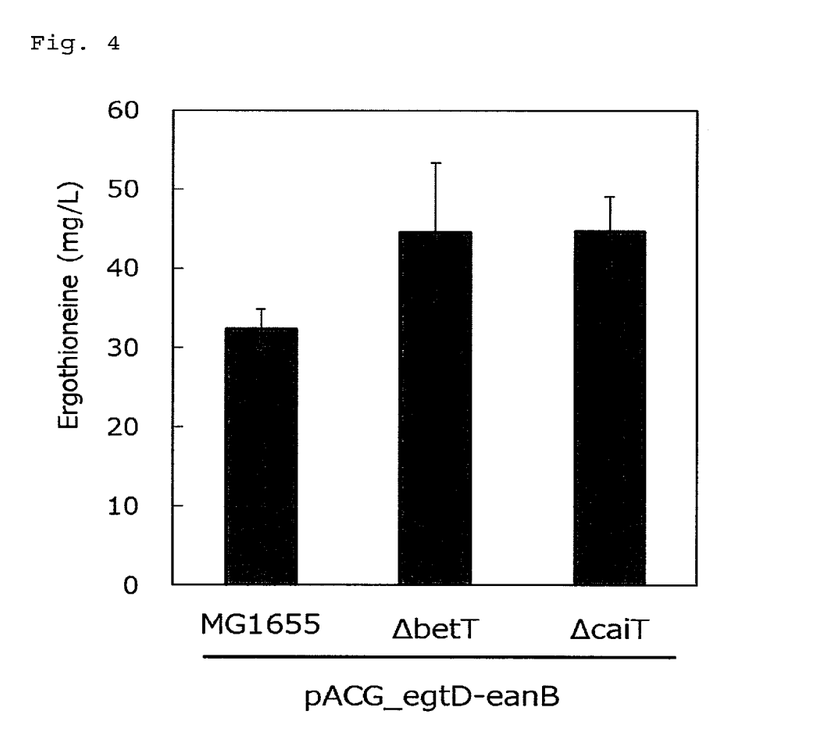
FIG. 4 is a graph showing the results of a test for ergothioneine fermentation production using a betT gene-disrupted strain and a caiT gene-disrupted strain, into which pACG_egtD-eanB was introduced, showing EGT production level accumulated in culture (48-hour culture) of MG1655, ΔbetT, and ΔcaiT strains transformed with pACG_egtD-eanB.

A production test using the prepared three strains was carried out using 10 mM sodium thiosulfate instead of 2.5 mM Cystine under the main culture conditions as described in Example 2. As a result, even when the egtD-eanB genes were used in the vector for EGT production, the EGT productivity was significantly improved in the ΔbetT and ΔcaiT strains at 48 hours after initiation of culture as compared to the wild strain (FIG. 4).

SEQ ID NO: 1 is the nucleotide sequence of the egt1 gene (SPBC1604.01) from *Schizosaccharomyces pombe*.

SEQ ID NO: 2 is the nucleotide sequence of the egt2 gene (SPBC660.12c) from *Schizosaccharomyces pombe*.

SEQ ID NO: 3 is the nucleotide sequence of a forward primer for amplifying the egt1 gene (SPBC1604.01) from *Schizosaccharomyces pombe*.

SEQ ID NO: 4 is the nucleotide sequence of a reverse primer for amplifying the egt1 gene (SPBC1604.01) from *Schizosaccharomyces pombe*.

SEQ ID NO: 5 is the nucleotide sequence of a forward primer for amplifying the egt2 gene (SPBC660.12c) from *Schizosaccharomyces pombe*.

SEQ ID NO: 6 is the nucleotide sequence of a reverse primer for amplifying the egt2 gene (SPBC660.12c) from *Schizosaccharomyces pombe*.

SEQ ID NO: 7 is the amino acid sequence common to core sequence regions.

SEQ ID NO: 8 is the amino acid sequence of a core sequence region.

SEQ ID NO: 9 is the amino acid sequence of a core sequence region.

SEQ ID NO: 10 is the amino acid sequence of a BetT protein.

SEQ ID NO: 11 is the amino acid sequence of a CaiT protein.

SEQ ID NO: 12 is the nucleotide sequence obtained by codon-optimizing the amino acid sequence of an EgtD protein from *Streptomyces coelicolor* for *Escherichia coli*.

SEQ ID NO: 13 is the nucleotide sequence obtained by codon-optimizing the amino acid sequence of an EanB protein from *Chlorobium limicola* for *Escherichia coli*.

INDUSTRIAL APPLICABILITY

A method for producing ergothioneine or a related substance thereof, or a mixture thereof, of the present invention allows for producing ergothioneine having various physiological activities such as a potent antioxidant activity at a low cost in large quantities.

The invention claimed is:

1. A method for producing ergothioneine or a related substance thereof having functionally related activity, or a mixture thereof, the method comprising:
   culturing a bacterium belonging to the family Enterobacteriaceae having an ergothioneine-producing ability in a culture medium, and
   collecting ergothioneine or a related substance thereof having functionally related activity, or a mixture thereof, from the culture medium or from cells obtained by culture,
   wherein the bacterium is modified so as to have a reduced activity of a BetT protein comprising an amino acid sequence having 90% or more identity to the amino acid sequence shown in SEQ ID NO: 10,
   wherein the bacterium produces ergothioneine or a related substance thereof having functionally related activity, and
   wherein the reduction of the activity is 50% or less than the activity of a corresponding protein of a parent strain of the bacterium.

2. The method of claim 1, wherein the amino acid sequence has 95% or more identity to the amino acid sequence shown in SEQ ID NO: 10.

3. The method of claim 1, wherein the bacterium belonging to the family Enterobacteriaceae having the ergothioneine-producing ability is a bacterium modified so as to enhance expression of ergothioneine biosynthesis genes.

4. The method of claim 3, wherein the ergothioneine biosynthesis genes comprise any one or more of a gene corresponding to egtA, egtB, egtC, egtD or egtE of *Mycobacterium smegmatis*, a gene corresponding to Egt1 Egt2 of *Schizosaccaromyces pombe*, a gene corresponding to Egt1 or Egt2 of *Neurospora crassa* and a gene corresponding to eanA or eanB of *Chlorobium limicola*.

5. The method of claim 1, wherein the bacterium belonging to the family Enterobacteriaceae having the ergothioneine-producing ability is a bacterium belonging to the genus *Escherichia*.

6. The method of claim 5, wherein the bacterium belonging to the family Enterobacteriaceae having the ergothioneine-producing ability is *Escherichia coli*.

7. The method of claim 4, wherein the ergothioneine biosynthesis genes comprise one or more genes corresponding to eanA or eanB of *Chlorobium limicola*.

* * * * *